United States Patent
Ketels et al.

(10) Patent No.: US 10,737,053 B2
(45) Date of Patent: Aug. 11, 2020

(54) OCCUPANT COMFORT SYSTEM

(71) Applicant: Faurecia Automotive Seating, LLC, Auburn Hills, MI (US)

(72) Inventors: Cedric Ketels, Holland, MI (US); Rod Goodrich, Watervliet, MI (US); Matthew K. Benson, Holland, MI (US); Alfred H. Bransdorfer, Holland, MI (US)

(73) Assignee: Faurecia Automotive Seating, LLC, Auburn Hills, MI (US)

( * ) Notice: Subject to any disclaimer, the term of this patent is extended or adjusted under 35 U.S.C. 154(b) by 342 days.

(21) Appl. No.: 15/836,001

(22) Filed: Dec. 8, 2017

(65) Prior Publication Data
US 2018/0161537 A1 Jun. 14, 2018

Related U.S. Application Data

(60) Provisional application No. 62/432,245, filed on Dec. 9, 2016.

(51) Int. Cl.
| | |
|---|---|
| *A61M 21/00* | (2006.01) |
| *B60W 50/00* | (2006.01) |
| *B60N 2/56* | (2006.01) |
| *B60N 2/66* | (2006.01) |
| *B60N 2/90* | (2018.01) |
| *B60N 2/00* | (2006.01) |
| *B60Q 3/70* | (2017.01) |

(Continued)

(52) U.S. Cl.
CPC .............. *A61M 21/00* (2013.01); *B60N 2/002* (2013.01); *B60N 2/5607* (2013.01); *B60N 2/66* (2013.01); *B60N 2/914* (2018.02); *B60N 2/99* (2018.02); *B60N 2/995* (2018.02); *B60Q 3/70* (2017.02); *B60Q 5/005* (2013.01); *B60W 40/10* (2013.01); *B60W 50/00* (2013.01); *A61M 2021/0005* (2013.01); *B60N 2002/0268* (2013.01); *B60N 2002/981* (2018.02); *B60Y 2302/03* (2013.01)

(58) Field of Classification Search
CPC .......... A61M 2021/0005; A61M 21/00; B60N 2002/0268; B60N 2/002; B60N 2/914; B60N 2/99
See application file for complete search history.

(56) References Cited

U.S. PATENT DOCUMENTS

| | | |
|---|---|---|
| 3,144,695 A | 8/1964 | Budwig |
| 3,341,903 A | 9/1967 | Buntic |

(Continued)

FOREIGN PATENT DOCUMENTS

| | | |
|---|---|---|
| CA | 2125642 | 12/1994 |
| CN | 1618654 | 5/2005 |

(Continued)

OTHER PUBLICATIONS

Office Action dated Apr. 19, 2019 for U.S. Appl. No. 15/852,010, 4552 US-U II pp. 1-6.

(Continued)

*Primary Examiner* — Christine H Matthews
(74) *Attorney, Agent, or Firm* — Barnes & Thornburg LLP

(57) ABSTRACT

A vehicle is adapted for movement along a roadway. A cabin of the vehicle is adapted for surrounding and supporting an occupant with movement of the vehicle. Systems of the vehicle control an environment within the cabin.

8 Claims, 9 Drawing Sheets

(51) Int. Cl.
  *B60Q 5/00*   (2006.01)
  *B60W 40/10*  (2012.01)
  *B60N 2/02*   (2006.01)

(56) References Cited

U.S. PATENT DOCUMENTS

| | | | |
|---|---|---|---|
| 3,632,076 | A | 1/1972 | Rogers, Jr. |
| 4,324,414 | A | 4/1982 | Wilkes |
| 4,432,525 | A | 2/1984 | Duvall |
| 4,500,062 | A | 2/1985 | Sandvik |
| 4,515,337 | A | 5/1985 | Torras |
| 4,685,730 | A | 8/1987 | Linguanotto |
| 4,727,629 | A | 3/1988 | Hoen |
| 4,869,554 | A | 9/1989 | Abu-Isa |
| 4,883,320 | A | 11/1989 | Izumida |
| 5,013,086 | A | 5/1991 | Benzur |
| 5,368,118 | A | 11/1994 | Hoefle |
| 5,393,126 | A | 2/1995 | Boulva |
| 5,558,399 | A | 9/1996 | Serber |
| 5,582,381 | A | 12/1996 | Graf |
| 5,769,490 | A | 6/1998 | Falzon |
| 5,921,605 | A | 7/1999 | Musukula |
| 5,976,097 | A | 11/1999 | Jensen |
| 5,992,933 | A | 11/1999 | West |
| 6,068,280 | A | 5/2000 | Torres |
| 6,793,289 | B2 | 9/2004 | Kuster |
| 6,814,407 | B2 | 11/2004 | Mundell |
| 7,044,553 | B2 | 5/2006 | Ropp |
| 7,063,386 | B2 | 6/2006 | Dowty |
| 7,083,233 | B2 | 8/2006 | Massara |
| 7,281,749 | B2 | 10/2007 | Yamada |
| 7,334,758 | B2 | 2/2008 | Williamson |
| 7,338,126 | B2 | 3/2008 | Ropp |
| 7,481,493 | B2 | 8/2008 | Fujita |
| 7,490,572 | B2 | 2/2009 | Grober |
| 7,506,910 | B2 | 3/2009 | Leitner |
| 7,517,024 | B2 | 4/2009 | Cvek |
| 7,575,206 | B2 | 8/2009 | Meier |
| 7,722,526 | B2 | 5/2010 | Kim |
| 7,731,294 | B2 | 6/2010 | Yasuda |
| 7,841,662 | B2 | 11/2010 | Samain |
| 7,971,939 | B2 | 7/2011 | Fujita |
| 8,020,933 | B2 | 9/2011 | Kim |
| 8,100,471 | B2 | 1/2012 | Lawall |
| 8,340,869 | B2 | 12/2012 | Wakita |
| 8,662,585 | B2 | 3/2014 | Garvis |
| 8,684,460 | B2 | 4/2014 | Weir, III |
| 8,690,750 | B2 | 4/2014 | Krueger |
| 8,840,186 | B2 | 9/2014 | Samain |
| 8,911,015 | B2 | 12/2014 | Cohen |
| 9,045,058 | B2 | 6/2015 | Katoh |
| 9,193,280 | B2 | 11/2015 | McMillen |
| 9,193,287 | B2 | 11/2015 | McMillen |
| 9,242,581 | B2 | 1/2016 | Farooq |
| 9,272,643 | B2 | 3/2016 | Nagayasu |
| 9,428,083 | B2 | 8/2016 | Lehner |
| 9,494,940 | B1 | 11/2016 | Kentley |
| 9,517,777 | B2 | 12/2016 | Hall |
| 9,550,440 | B2 | 1/2017 | Nagayasu |
| 9,561,741 | B2 | 2/2017 | Nagayasu |
| 9,604,560 | B1 | 3/2017 | Ellis |
| 9,682,682 | B2 | 6/2017 | Aoki |
| 9,713,380 | B2 | 7/2017 | Gehner |
| 9,751,434 | B2 | 9/2017 | Sugiyama |
| 9,802,513 | B2 | 10/2017 | Katoh |
| 9,950,646 | B2 | 4/2018 | Katoh |
| 9,975,458 | B2 | 5/2018 | Takeuchi |
| 2001/0029621 | A1 | 10/2001 | Howland |
| 2002/0060493 | A1 | 5/2002 | Nishino |
| 2002/0135214 | A1 | 9/2002 | Ursel |
| 2003/0116999 | A1 | 6/2003 | Fujita |
| 2004/0245824 | A1 | 12/2004 | McMillen |
| 2005/0179294 | A1 | 8/2005 | Dowty |
| 2006/0055214 | A1 | 3/2006 | Serber |
| 2006/0138831 | A1 | 6/2006 | McMillen |
| 2006/0191114 | A1 | 8/2006 | Yu |
| 2007/0080013 | A1 | 4/2007 | Melz |
| 2008/0023995 | A1 | 1/2008 | Ott |
| 2009/0115234 | A1 | 5/2009 | Samain |
| 2009/0188698 | A1 | 7/2009 | Cloutier |
| 2010/0050923 | A1 | 3/2010 | Lemons |
| 2010/0268133 | A1 | 10/2010 | Samain |
| 2011/0099773 | A1 | 5/2011 | Golden |
| 2013/0006478 | A1 | 1/2013 | Lin |
| 2013/0175838 | A1 | 7/2013 | Oshima |
| 2015/0105641 | A1 | 4/2015 | Austin |
| 2015/0266448 | A1 | 9/2015 | Aoki |
| 2015/0343924 | A1 | 12/2015 | Takeuchi |
| 2016/0096450 | A1 | 4/2016 | Kondrad |
| 2016/0159254 | A1 | 6/2016 | Katoh |
| 2016/0243967 | A1 | 8/2016 | Seibold |
| 2017/0129373 | A1 | 5/2017 | Knox |
| 2017/0253254 | A1* | 9/2017 | Sweeney ............... B60W 50/16 |
| 2018/0222518 | A1 | 8/2018 | Hill |

FOREIGN PATENT DOCUMENTS

| | | |
|---|---|---|
| CN | 101274604 | 10/2008 |
| CN | 104758153 | 7/2015 |
| DE | 10041910 | 1/2002 |
| DE | 102004058503 | 1/2006 |
| DE | 102009048902 | 4/2011 |
| DE | 102011109470 | 2/2012 |
| DE | 102011009211 A1 | 7/2012 |
| DE | 102015117980 | 5/2016 |
| EP | 0185388 A1 | 6/1986 |
| EP | 1193117 | 4/2002 |
| EP | 1663727 | 6/2006 |
| FR | 2061931 | 6/1971 |
| FR | 2776583 | 10/1999 |
| GB | 1330683 A | 9/1973 |
| GB | 8816607 | 8/1988 |
| GB | 2206787 | 1/1989 |
| GB | 2206787 B | 1/1989 |
| GB | 2407028 | 4/2005 |
| GB | 201307595 | 6/2013 |
| JP | 2003299231 A | 10/2003 |
| WO | 2004026080 | 4/2004 |
| WO | 2005025945 | 3/2005 |
| WO | 2005037020 | 4/2005 |
| WO | 2005094632 | 10/2005 |
| WO | 2006083158 | 8/2006 |
| WO | 2006095455 A1 | 9/2006 |
| WO | 2016197068 | 12/2016 |

OTHER PUBLICATIONS

Extended European Search Report for European App. No. 17206306.7 dated May 14, 2018, 4175 EP || 5 pages.

Office Action dated Nov. 7, 2019 for U.S. Appl. No. 15/846,342, 4510 US-U || (pp. 1-6).

Office Action dated Feb. 15, 2019 for U.S. Appl. No. 15/856,341 (pp. 1-10).

German Office Action for German App. No. 10 2016 123 681.0 dated Oct. 19, 2017, 601-666 DE, 5 pages, (no English translation available).

* cited by examiner

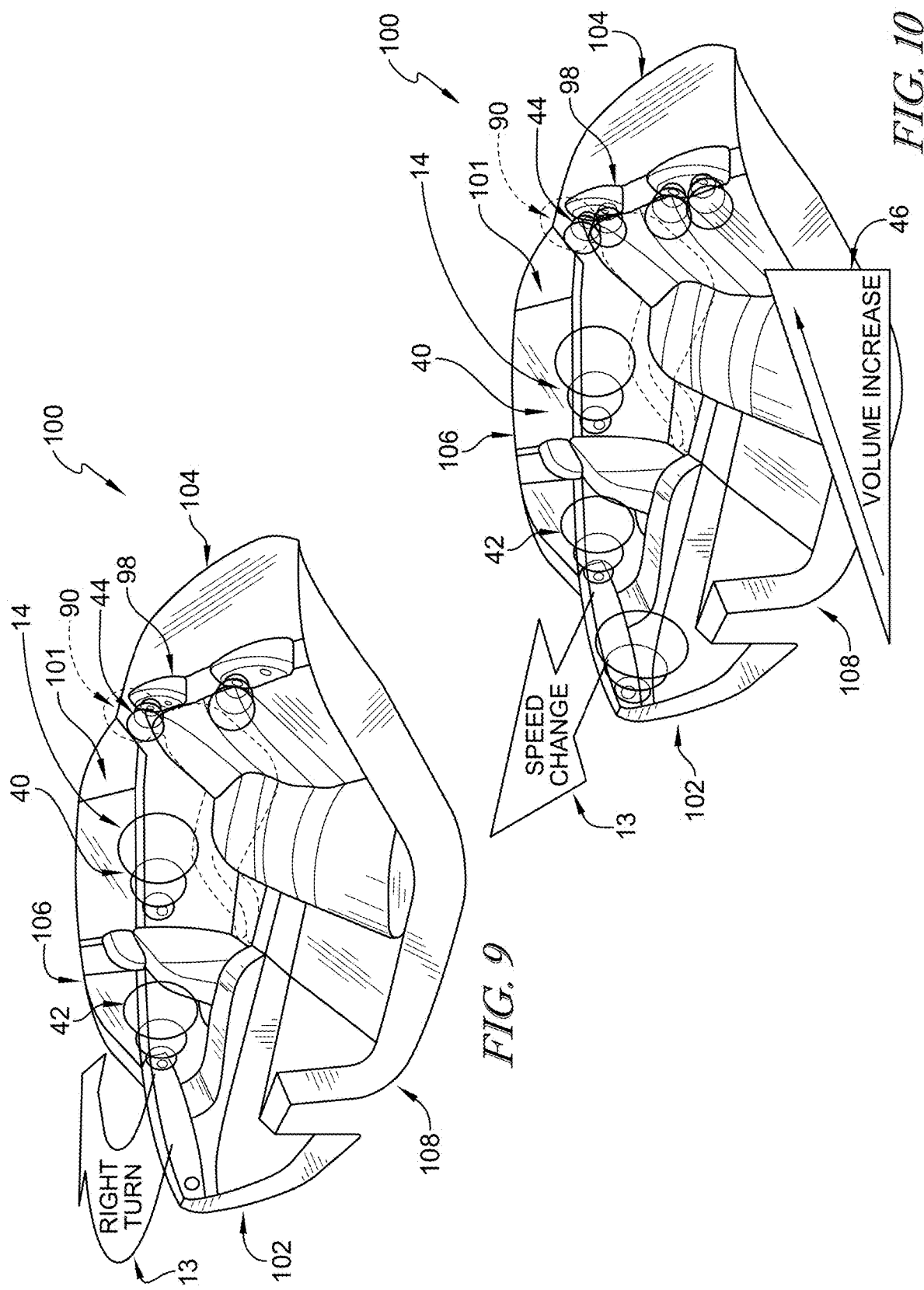

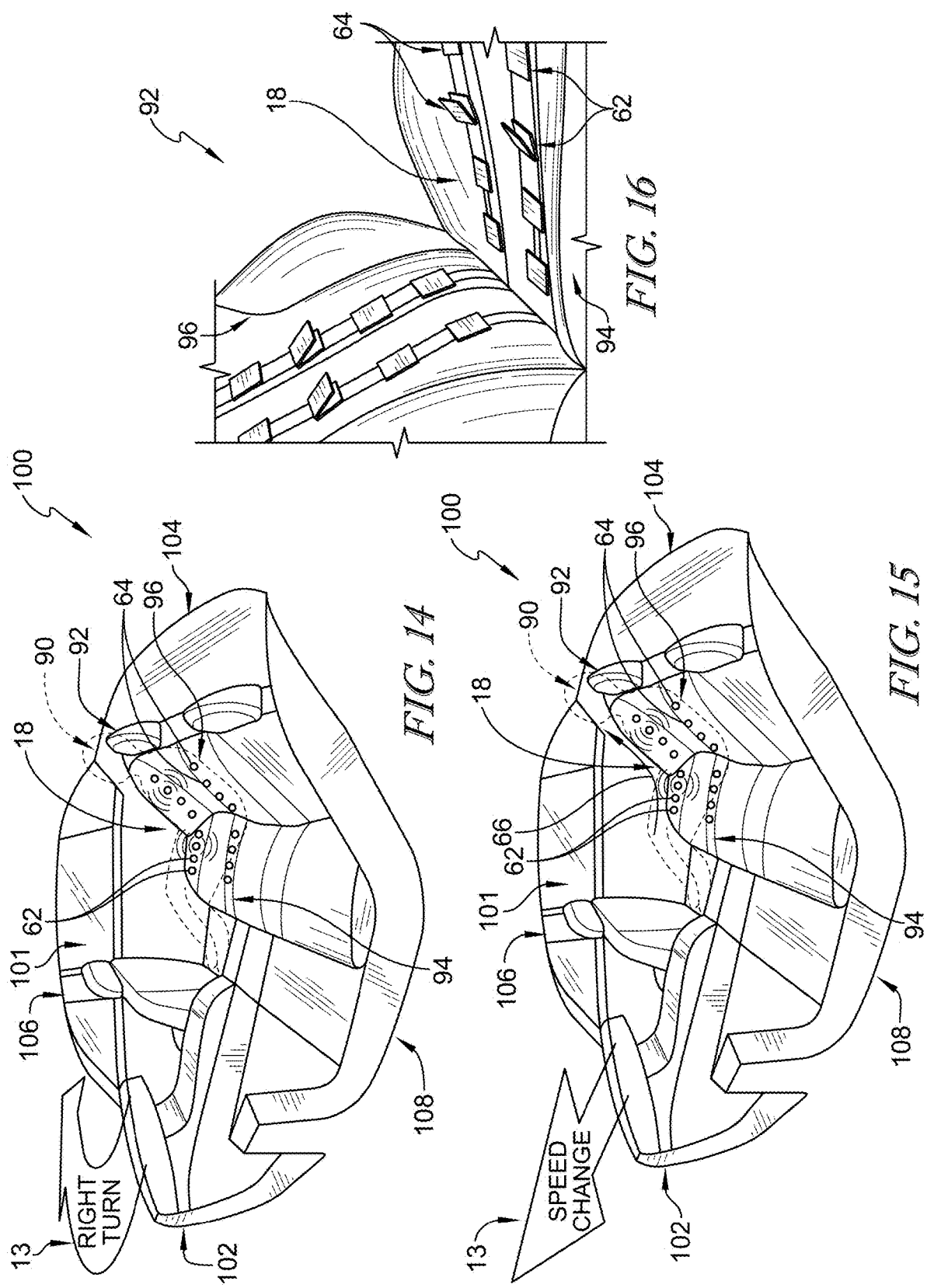

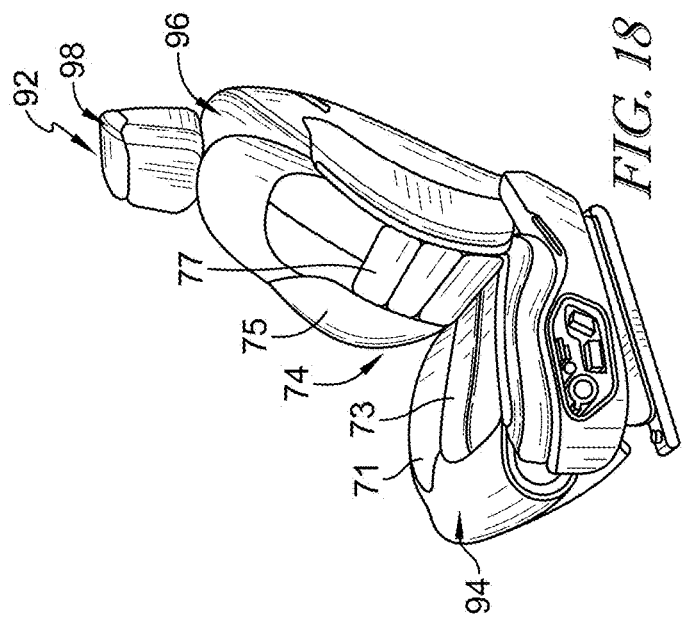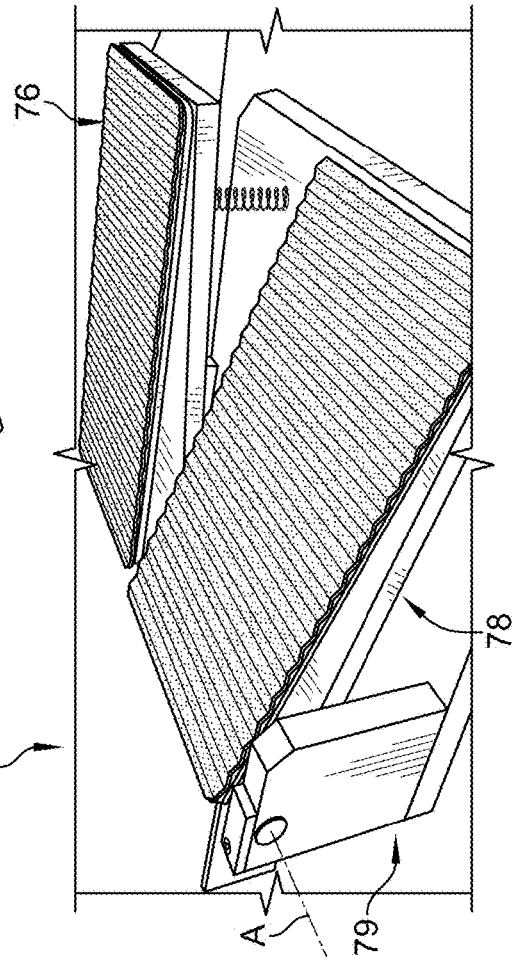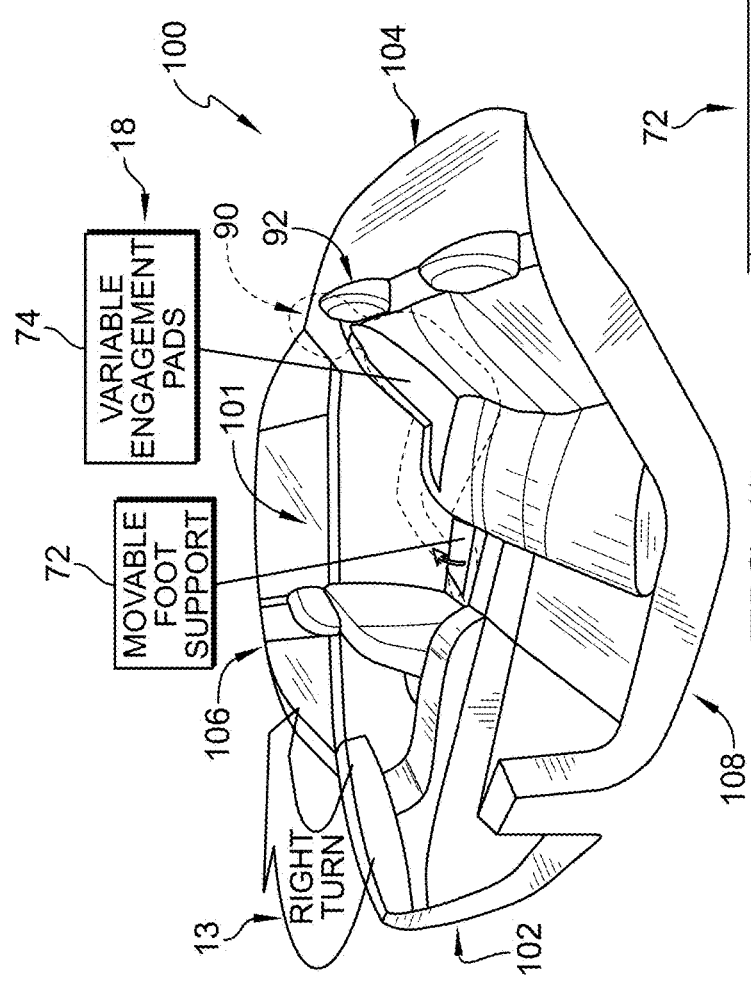

US 10,737,053 B2

OCCUPANT COMFORT SYSTEM

PRIORITY CLAIM

This application claims priority under 35 U.S.C. § 119(e) to U.S. Provisional Application Ser. No. 62/432,245, filed Dec. 9, 2016, which is expressly incorporated by reference herein.

BACKGROUND

The present disclosure relates to vehicle systems. More particularly, the present disclosure relates to vehicle systems for use in providing a comfortable environment for an occupant of the vehicle.

SUMMARY

According to the present disclosure, a vehicle is adapted for movement along a roadway. A cabin of the vehicle is adapted for surrounding and supporting an occupant during movement of the vehicle. Systems of the vehicle control an environment within the cabin.

In illustrative embodiments, a motion-sickness mitigation system includes a control system and a sensory feedback system. The control system monitors for motion inputs to identify changes in movement of the vehicle. The control system is configured to produce a signal indicative of the change in movement. The sensory feedback system generates at least one of a tactile, visual, audial, and olfactory alert indicative of the change in movement to inform an occupant of the vehicle of the change in movement in response to receiving the signal from the control system to reduce a likelihood of the occupant becoming motion-sick.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which.

Figure 1:
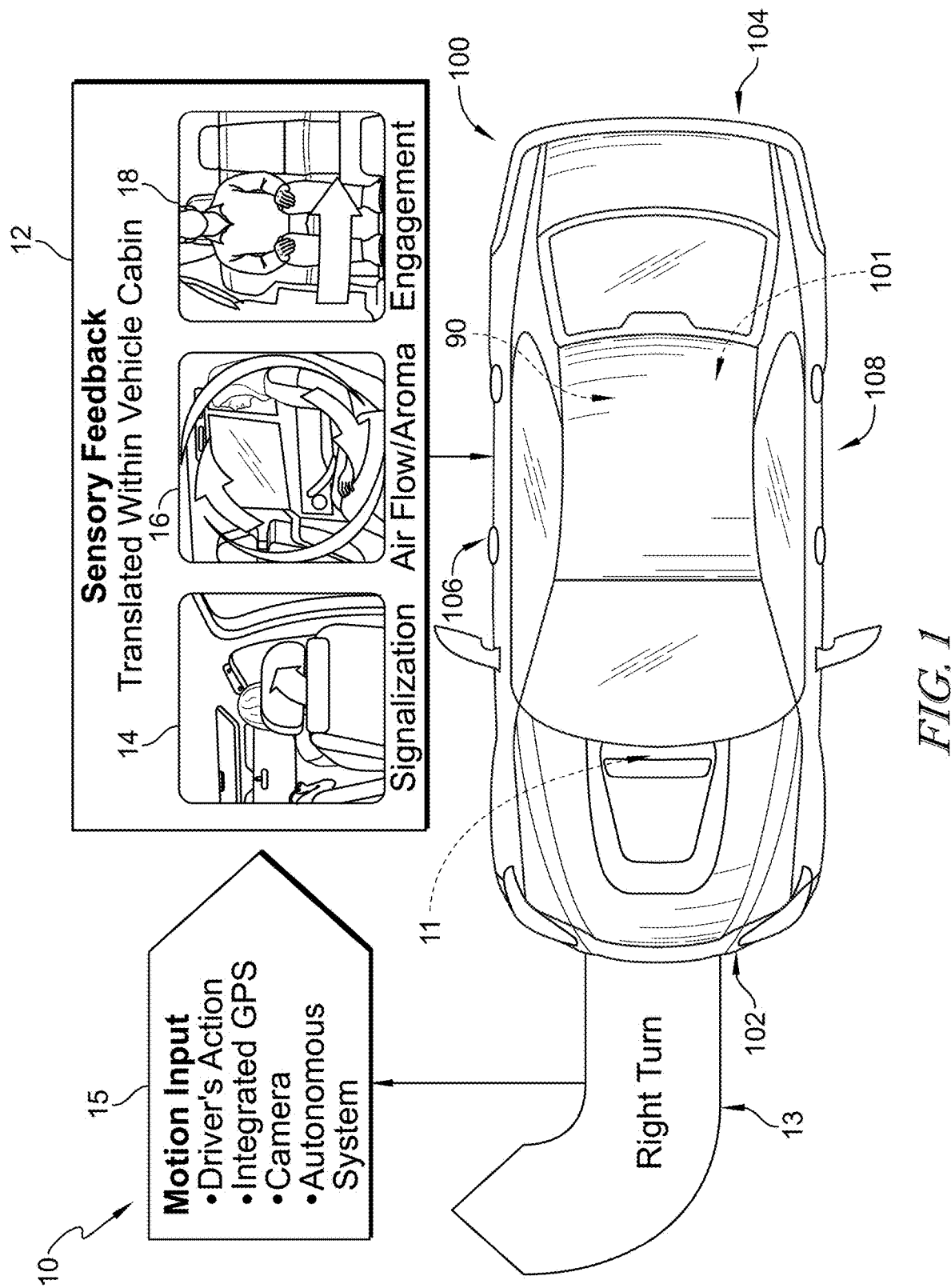
FIG. 1 is a diagrammatic view of a motion-sickness mitigation system used to increase comfort of an occupant in a cabin of a vehicle by providing sensory feedback to the occupant in response to motion input of the vehicle to alert the occupant to changes in motion of the vehicle to reduce a likelihood that the occupant becomes motion-sick due to changes in movement of the vehicle.
Figure 4:
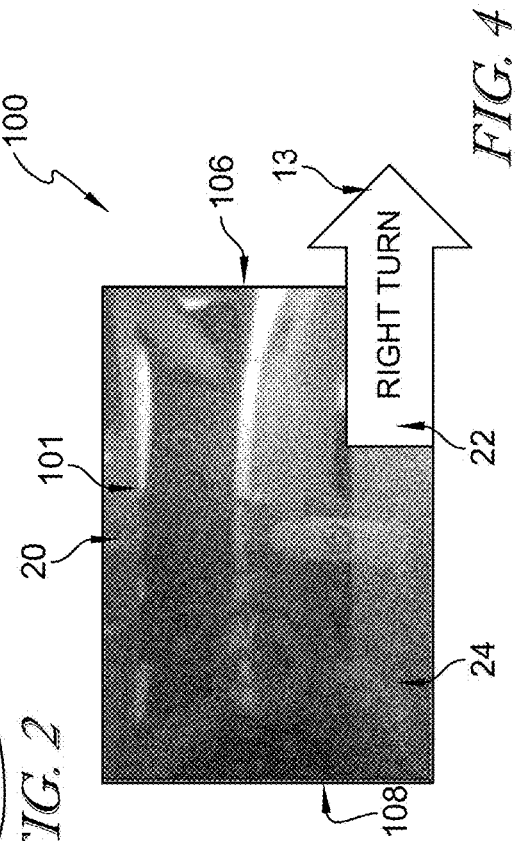
Figure 3:
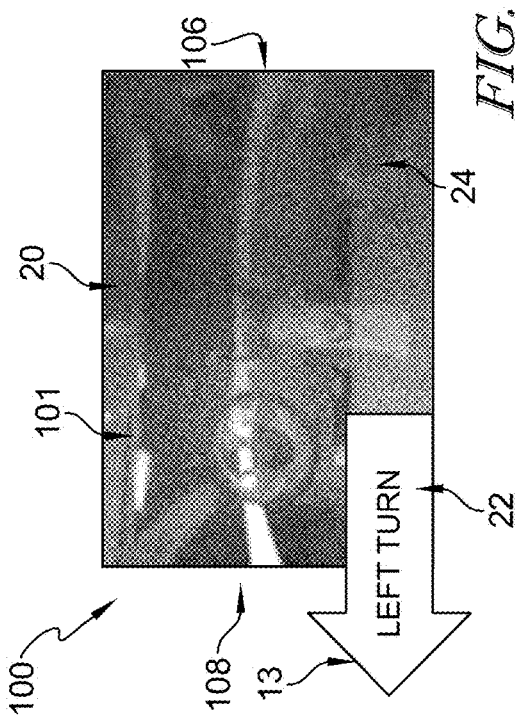
Figure 5:
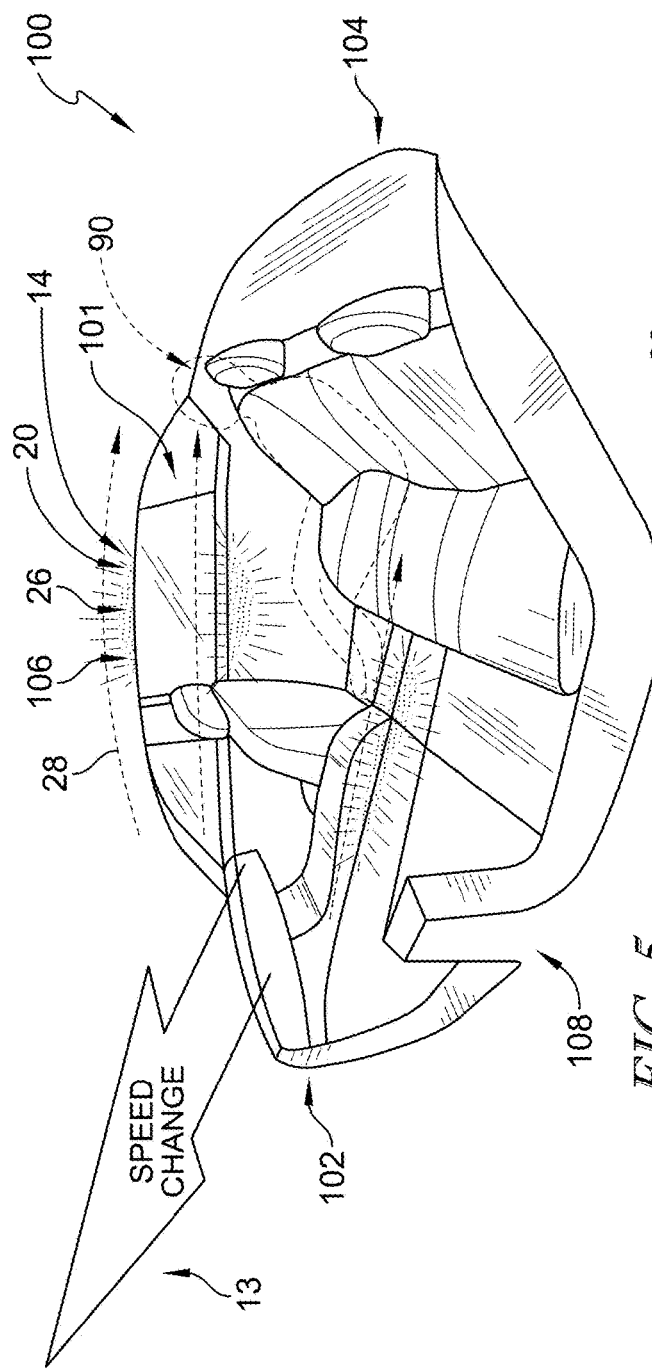
Figure 6:
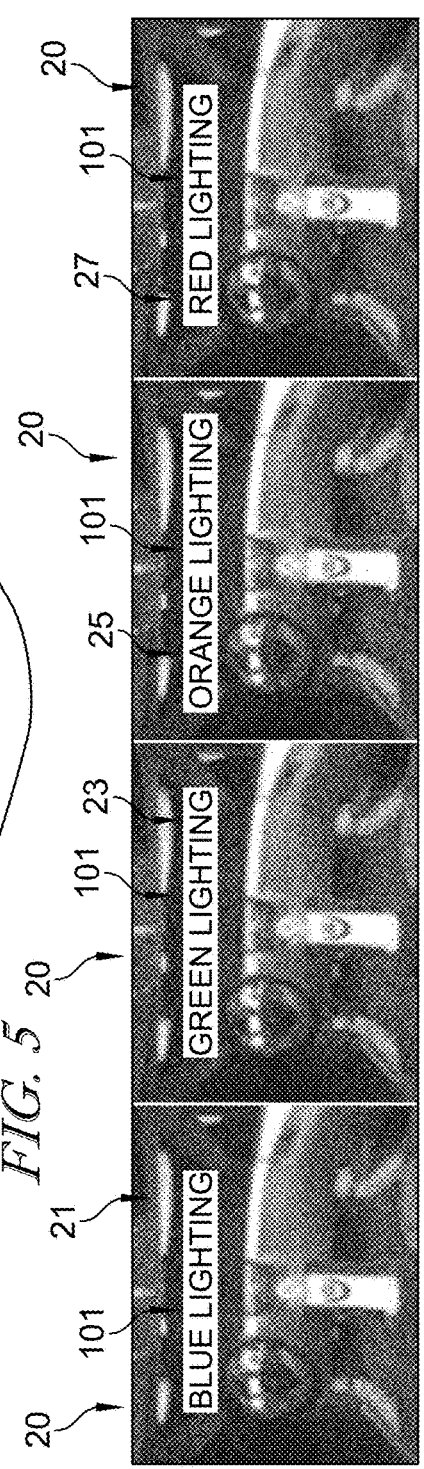
Figure 8:
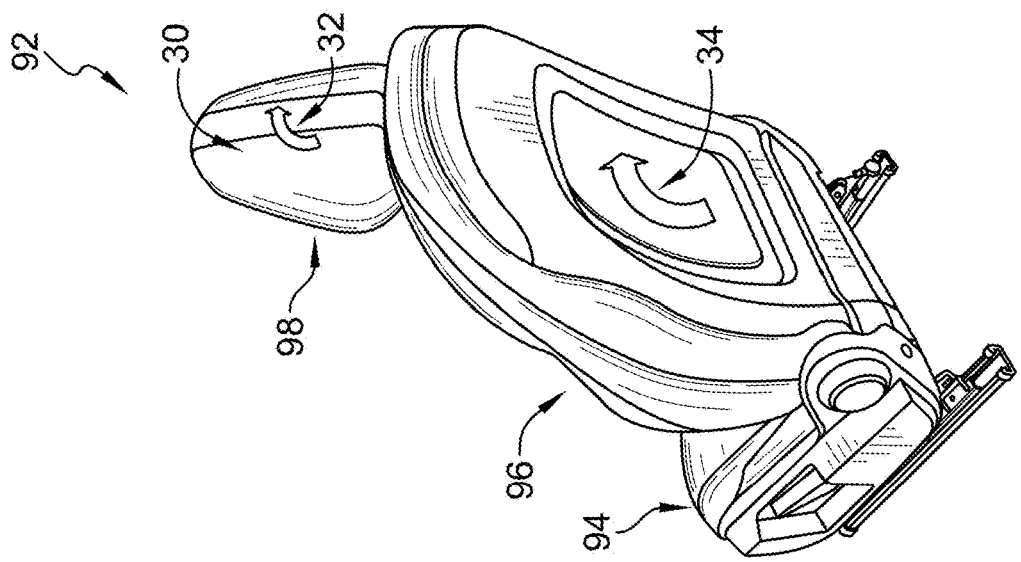
Figure 7:
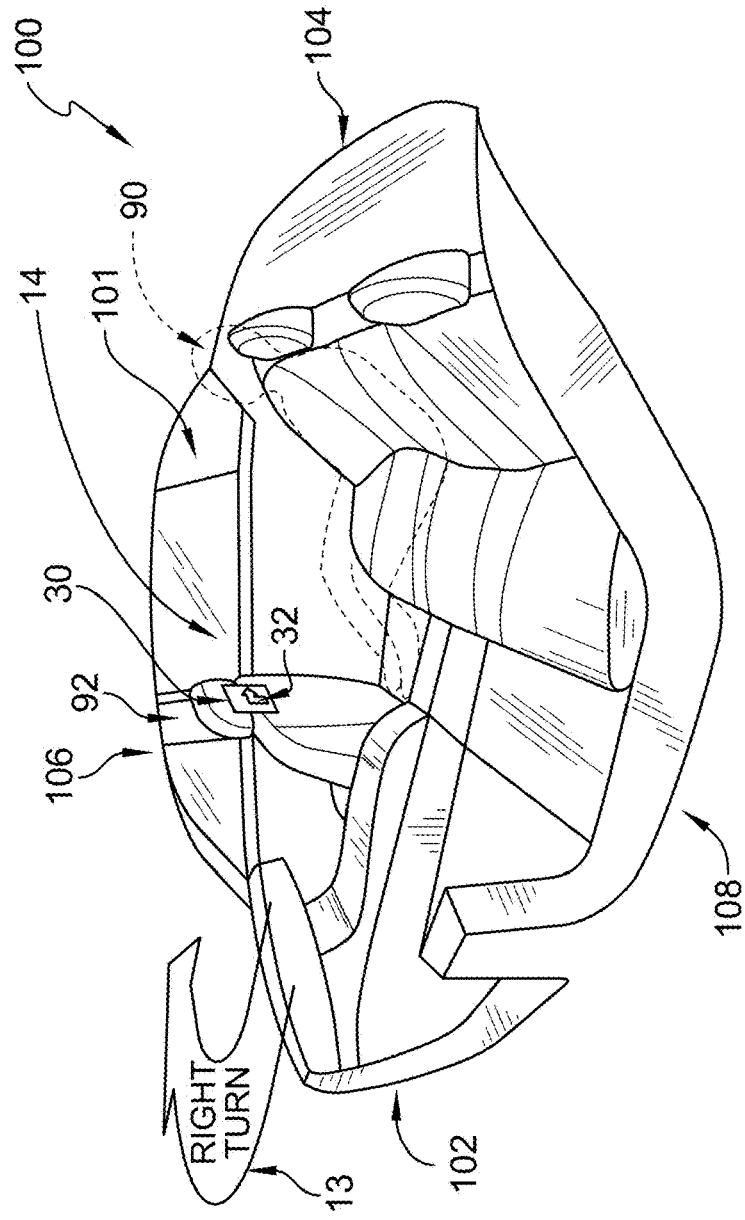
Figure 11:
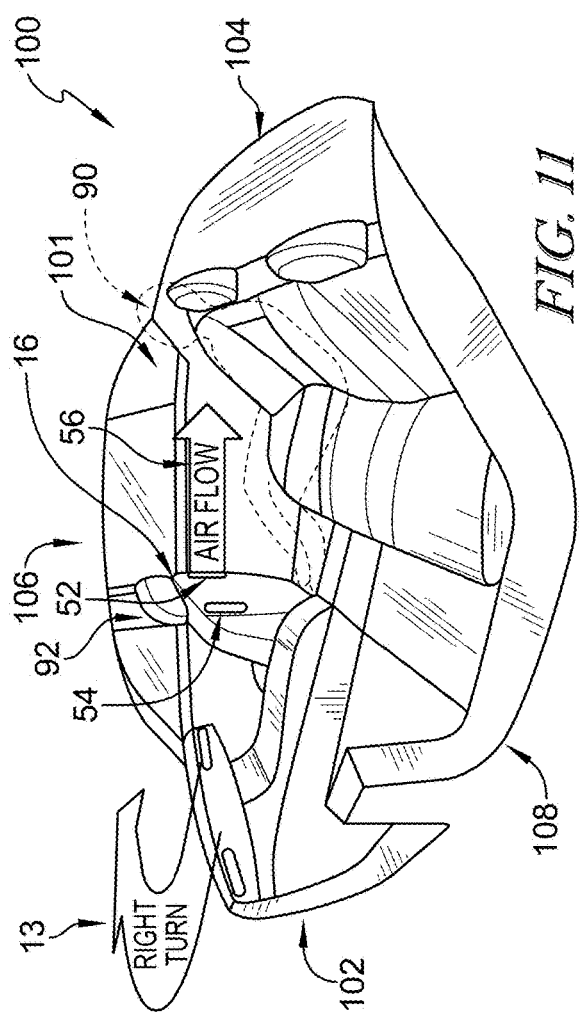
Figure 12:
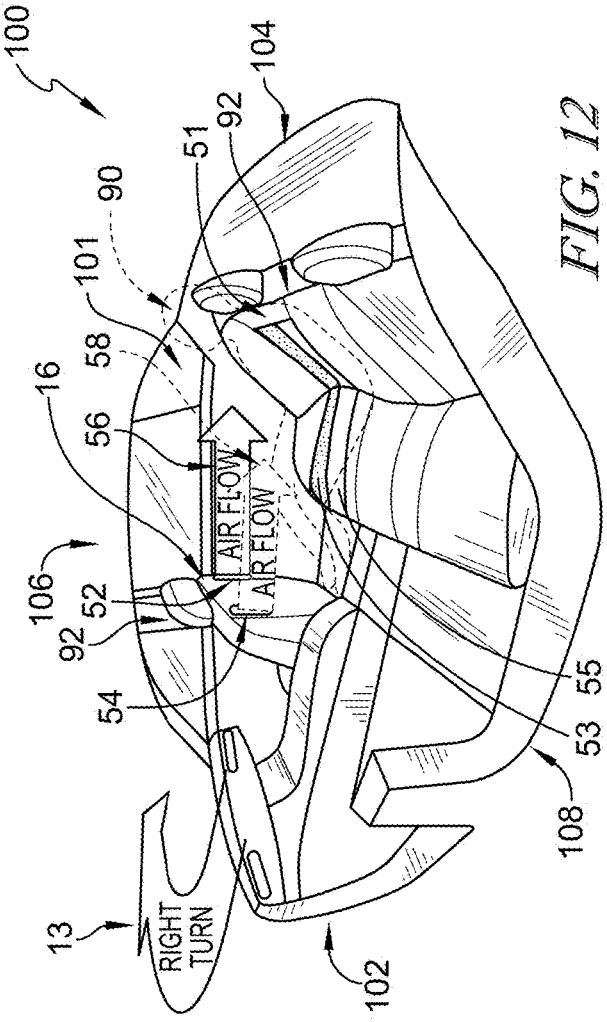
Figure 13:
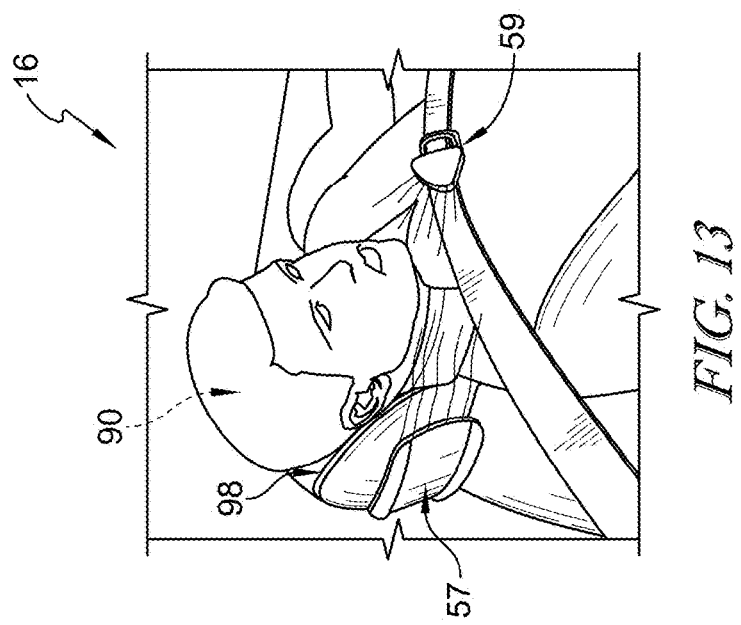
Figure 20:
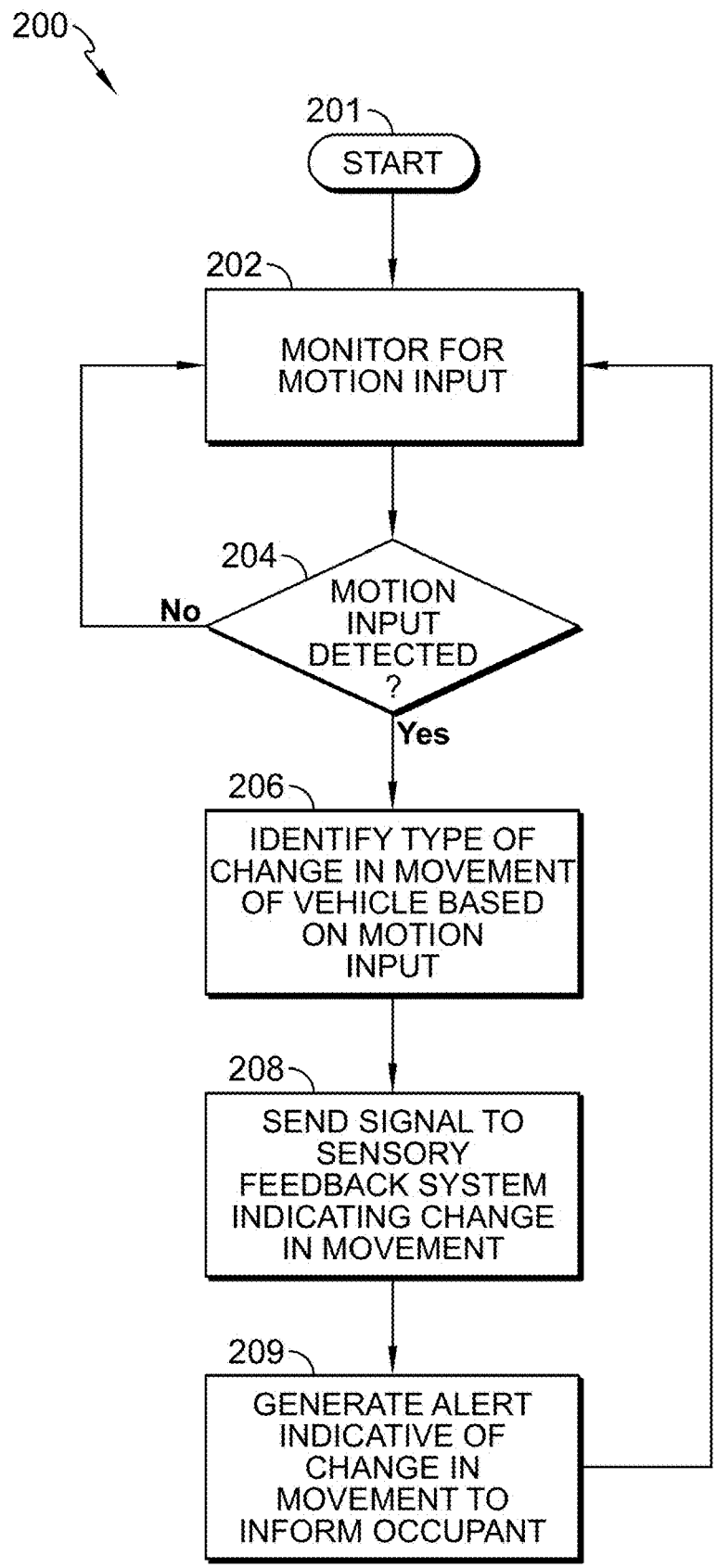

FIG. 3 is a diagrammatic and perspective view of another embodiment of a process for providing sensory feedback in the vehicle of FIG. 1 showing the right-side portion of the cabin dimmed compared to a left-side portion of the cabin and suggesting that the right-side portion of the cabin becomes dimmed in response to an input of the vehicle signaling a left turn in order to indicate the change in movement to the occupant;

FIG. 4 is view similar to FIG. 3 showing the left-side portion of the cabin dimmed compared to the right-side portion of the cabin and suggesting that the left-side portion of the cabin becomes dimmed in response to an input of the vehicle signaling a right turn in order to indicate the change in movement to the occupant;

FIG. 5 is a diagrammatic and perspective view of another embodiment of a process for providing sensory feedback in the vehicle of FIG. 1 showing portions of the cabin illuminated and suggesting that illumination moves from a front of the cabin toward a rear of the cabin in response to an input of the vehicle signaling an increase in speed in order to indicate the change in movement to the occupant;

FIG. 6 is a diagrammatic and perspective view of another embodiment of a process for providing sensory feedback in the vehicle of FIG. 1 showing the cabin illuminated in a first color and suggesting that the illumination changes colors in response to an input of the vehicle signaling an increase in speed in order to indicate the change in movement to the occupant;

FIG. 7 is a diagrammatic and perspective view of another embodiment of a process for providing sensory feedback in the vehicle of FIG. 1 showing a right-turn arrow displayed on a monitor attached to a forward vehicle seat in the cabin and suggesting that the right-turn arrow is displayed on the monitor in response to an input of the vehicle signaling a right turn in order to indicate the change in movement to the occupant;

FIG. 8 is a perspective view of a vehicle seat of the vehicle in FIG. 1 showing illuminated arrows on a seat back and head rest of the vehicle seat and suggesting that that the arrows become illuminated in response to an input of the vehicle signaling a turn in order to indicate the change in movement to the occupant;

FIG. 9 is a diagrammatic and perspective view of another embodiment of a process for providing sensory feedback in the vehicle of FIG. 1 showing a sound system of the cabin and suggesting that the sound system produces sound along the right-side portion of the cabin and right-side portions of the head rests in response to an input of the vehicle signaling a right turn in order to indicate the change in movement to the occupant;

FIG. 10 is a diagrammatic and perspective view of another embodiment of a process for providing sensory feedback in the vehicle of FIG. 1 showing the sound system of the cabin and suggesting that the sound system produces sound of increasing volume in response to an input of the vehicle signaling an increase in speed in order to indicate the change in movement to the occupant;

FIG. 11 is a diagrammatic and perspective view of another embodiment of a process for providing sensory feedback in the vehicle of FIG. 1 showing that fans are included in the forward vehicle seat and suggesting that air flow is produced by a right-side fan toward the occupant in response to an input of the vehicle signaling a right turn in order to indicate the change in movement to the occupant;

FIG. 12 is a view similar to FIG. 11 showing that a variable-temperature mat is included in an occupant support surface of the rear vehicle and suggesting that relatively warmer air flow is produced by a right-side fan than a left-side fan toward the occupant and a right-side of the mat is relatively warmer than a left-side in response to an input of the vehicle signaling a right turn in order to indicate the change in movement to the occupant;

FIG. 13 is a perspective view of the occupant in a vehicle seat of the vehicle of FIG. 1 showing that one or more fan ducts are included in a headrest of the vehicle seat and that a fan is included on a restraint of the vehicle and suggesting that the air flow is produced by the fan ducts and fan of the restraint to indicate changes in vehicle movement to the occupant;

FIG. 14 is a diagrammatic and perspective view of another embodiment of a process for providing sensory feedback in the vehicle of FIG. 1 showing motion points included in the support surface the rear vehicle seat and suggesting that motion points along a right-side portion of the vehicle seat engage with the occupant in response to an input of the vehicle signaling a right turn in order to indicate the change in movement to the occupant;

FIG. 15 is a view similar to FIG. 14 showing the motion points of the vehicle seat and suggesting that the motion points engage with the occupant from front to back in response to an input of the vehicle signaling an increase in speed in order to indicate the change in movement to the occupant;

FIG. 16 is a perspective view of one embodiment of a vehicle seat showing that the vehicle seat includes a seat bottom and a seat back and that motion points in the form of inflatable bladders are included along the seat bottom and seat back;

FIG. 17 is a diagrammatic and perspective view of another embodiment of a process for providing sensory feedback in the vehicle of FIG. 1 showing that variable engagement pads are included in the occupant support surface of the rear vehicle and that a movable foot support is positioned on a floor of the vehicle and suggesting that variable engagement pads along a right side of the vehicle seat increase engagement with the occupant and the movable foot support tilts toward a right side of the vehicle in response to an input of the vehicle signaling a right turn in order to indicate the change in movement to the occupant;

FIG. 18 is a perspective view of one embodiment of a vehicle seat showing that the vehicle seat includes a seat bottom and a seat back and that variable engagement pads are included in right-side and left-side bolsters of the seat bottom and seat back and in central portions of the seat bottom and seat back;

FIG. 19 is a perspective view of one embodiment of a movable foot support showing that the movable foot support includes two independently adjustable pedals that move relative to a base; and FIG. 20 is a diagrammatic view of one embodiment of a process for providing sensory feedback in the vehicle of FIG. 1.

DETAILED DESCRIPTION

A motion-sickness mitigation system 10 in accordance with the present disclosure is adapted for use in a vehicle 100 as shown in FIG. 1. Motion-sickness mitigation system 10 is configured to increase comfort of an occupant 90 in a cabin 101 of vehicle 100 by providing sensory feedback to occupant 90 in response to motion inputs 15 of vehicle 100 to alert occupant 90 to changes in movement 13 of vehicle 100, such as a right turn, to reduce a likelihood that occupant 90 becomes motion-sick due to changes in movement 13 of vehicle 100. For example, a sensory feedback system 12 includes at least one of a signalization system 14 (FIGS. 2-10), an air flow system 16 (FIGS. 11-13), and an engagement system 18 (FIGS. 14-19) to generate one or more of a tactile, visual, audial, and olfactory alert indicative of change in movement 13 of vehicle 100 to inform occupant 90. One embodiment of a process 200 for generating the alerts is shown in FIG. 20.

Motion-sickness mitigation system 10 includes a control system 11 and sensory feedback system 12 as shown in FIG. 1. Control system 11 is configured to identify changes in movement 13 (such as a right turn) of vehicle 100 based on motion inputs 15 detected by control system 11. In some embodiments, control system 11 is integrated with other systems used to control operation of vehicle 100.

In the illustrative embodiment, motion inputs 15 include at least one of a concurrent, an anticipated, or an instructed change in movement 13 of vehicle 100 as suggested in FIG. 1. For example, a driver input, such as turning a steering wheel or depressing a brake pedal of vehicle 100, generates a concurrent change in movement 13 of vehicle 100. Integrated systems of vehicle 100, such as a GPS or camera, can anticipate changes in movement 13. Other integrated systems of vehicle 100, such as an autonomous driving system, can instruct changes in movement 13 of vehicle 100 during an autonomous driving mode of vehicle 100.

Control system 11 identifies a type of change in movement 13 of vehicle 100, such as a right turn, a left turn, acceleration, or deceleration, and sends a signal to sensory feedback system 12 indicating change in movement 13 as suggested in FIG. 1. Sensory feedback system 12 in accordance with the present disclosure includes at least one of a signalization system 14, an air flow system 16, and an engagement system 18 to generate one or more alerts within cabin 101 indicative of change in movement 13 to inform occupant 90.

Figure 2:
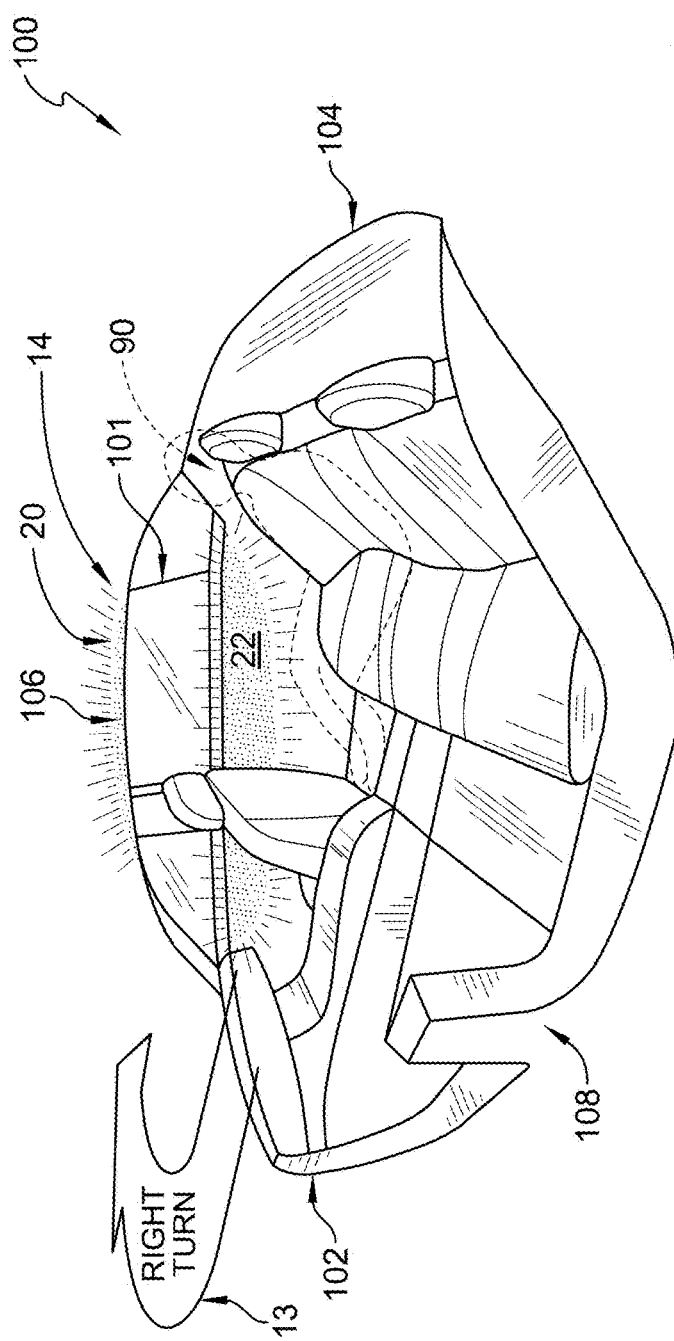
FIG. 2 is a diagrammatic and perspective view of one embodiment of a process for providing sensory feedback in the vehicle of FIG. 1 showing a right-side portion of the cabin illuminated and suggesting that the right-side portion of the cabin becomes illuminated in response to an input of the vehicle signaling a right turn in order to indicate the change in movement to the occupant.

Signalization system 14 in accordance with the present disclosure can include one or more of a lighting system 20, indicator system 30, and sound system 40 to produce various types of alerts to inform occupant 90 of changes in motion 13 as suggested in FIGS. 2-10. In one illustrative embodiment, lighting system 20 is configured to produce an illuminated portion 22 of cabin 101 to inform occupant 90 of change in movement 13 as shown in FIG. 2. For example, illuminated portion 22 extends along a right side 106 of cabin 101 indicative of a right turn of vehicle 100 as shown in FIG. 2. Similarly, lighting system 20 is configured to produce an illuminated portion 22 along a left side 108 of cabin 101 indicative of a left turn of vehicle 100. In some embodiments, lighting system 20 is also configured to produce a dimmed portion 24 along an opposite side of cabin 101 from illuminated portion 22 as suggested in FIGS. 3 and 4. In some embodiments, illuminated portion 22 and/or dimmed portion 24 extend from a front 102 of cabin 101 to a rear 104 of cabin 101 to inform occupants 90 sitting in front-row seats and in back-row seats of vehicle 100 of change in movement 13.

In another illustrative embodiment, lighting system 20 is configured to produce one or more moving points of illumination 26 to inform occupant 90 of change in movement 13 as suggested in FIG. 5. For example, points of illumination 26 move along cabin 101 from front 102 to rear 104 in a direction 28 to inform occupant 90 of acceleration of vehicle 100. Similarly, points of illumination can move from rear 104 to front 102 to inform occupant 90 of deceleration of vehicle 100. In yet another illustrative embodiment, lighting system 20 can produce an illuminated portion 22 along front 102 (indicative of acceleration) or rear 104 (indicative of deceleration) of cabin 101.

In yet another illustrative embodiment, lighting system 20 is configured to produce illumination of various colors to inform occupant 90 of changes in speed as suggested in FIG. 6. For example, lighting system 20 can illuminate cabin 101 with blue lighting 21 at low speeds, and illuminate cabin 101 with "warmer" colors (i.e., having a relatively longer wavelength in the electromagnetic spectrum) such as green 23, orange 25, and red 27, as the speed of vehicle 100 increases.

In some embodiments, cabin 101 is illuminated with first color indicating a steady-state in speed of vehicle 100, and illuminated with increasingly "cooler" colors (i.e., having relatively shorter wavelengths in the electromagnetic spectrum) to indicate deceleration or increasingly "warmer" colors to indicate acceleration of vehicle 100. In some embodiments, lighting system 20 is configured to produce various types of illumination within cabin 101, such as in a gradient pattern, gradually intensifying or subsiding brightness, pulsing or blinking, and color variations, among others.

In one illustrative embodiment, indicator system 30 is configured to produce indicia 32 visible to occupant 90 that is indicative of change in movement 13 as shown in FIG. 7. For example, indicator system 30 is configured to display a right curving arrow to inform occupant 90 of a right turn of vehicle 100. Similarly, indicator system 30 is configured to display a left curving arrow, an upward extending arrow, or a downward extending arrow to inform occupant 90 of a left turn, acceleration, or deceleration of vehicle 100, respectively. In some embodiments, indicator system is in the form of a monitor coupled to a front-row seat, such as vehicle seat 92 in FIG. 7. In some embodiments, a monitor is arranged in front of each seating position within cabin 101 as part of indicator system 30. While the indicia is shown in the form of stylized arrows, other forms of indicia are contemplated, such as a compass-style dial, moving graphics, patterns, and other forms of indicia useful for informing occupant 90 of changes in motion 13.

In another illustrative embodiment, indicator system 30 is integrated into vehicle seat 92 as suggested in FIG. 8. Vehicle seat 92 includes a seat bottom 94, a seat back 96 extending upward from seat bottom 94, and a head rest 98 attached to seat back 96. Indicator system 30 can produce one or more indicia 32, 34 in head rest 98 and seat back 96. In some embodiments, indicia 32, 34 are produced by an array of lights positioned inside vehicle seat 92 that illuminate in a pattern to form indicia 32, 34.

In one illustrative embodiment, sound system 40 is configured to produce sound waves 42 within cabin 101 that are indicative of change in movement 13 as shown in FIG. 9. For example, sound system 40 is configured to produce sound waves 42 along right side 106 of cabin 101 to inform occupant 90 of a right turn of vehicle 100. Similarly, sound system 40 is configured to produce sound waves 42 along left side 108 of cabin 101 indicative of a left turn of vehicle 100. In some embodiments, sound system 40 is integrated into an audio entertainment system of vehicle 100. In some embodiments, sound waves 42 are audible to occupant 90. In some embodiments, sound waves 42 create tactile pressure or vibration against occupant 90. In some embodiments, speakers are integrated into head rests 98, and sound waves 44 are produced thereby to alert occupant 90 to changes in motion 13.

In another illustrative embodiment, sound system 40 is configured to produce sound waves 42, 44 of increasing volume to indicate acceleration of vehicle 100 as shown in FIG. 10. Similarly, sound system 40 is configured to produce sound waves 42, 44 of decreasing volume to indicate deceleration of vehicle 100. In some embodiments, sound system 40 is configured to produce various types of audible and/or tactile sound waves 42, 44 in cabin 101, such as in a gradient pattern, gradually intensifying or subsiding volume, and pulsing, among others. In some embodiments, sound system 40 is configured to produce audible sound waves that mimic sounds produced by vehicles during various changes in motion, such as the screech of tires when turning.

One embodiment of air flow system 16 in accordance with the present disclosure is shown in FIG. 11. Air flow system 16 is configured to produce air flow toward occupant 90 indicative of change in movement 13. Air flow system 16 includes a right-side fan 52 and a left-side fan 54. In one illustrative embodiment, right-side fan 52 is configured to produce an air flow 56 along a right side of occupant 90 to inform occupant 90 of a right turn of vehicle 100. Similarly, left-side fan 54 is configured to produce an air flow along a left side of occupant 90 to inform occupant 90 of a left turn of vehicle 100. In some embodiments, air flow system 16 is configured to produce air flows of increasing or decreasing volume toward occupant 90 to indicate acceleration or deceleration of vehicle 100, respectively. In some embodiments, air flow system 16 is configured to produce a variety of aromas, such as lavender or ginger, to reduce a likelihood of motion sickness in occupant 90.

In another illustrative embodiment, air flow system 16 is configured to produce air flows having different temperatures to indicate change in movement 13 to occupant 90 as suggested in FIG. 12. For example, right-side fan 52 is configured to produce an air flow 56 along a right side of occupant 90 having a first temperature and left-side fan 54 is configured to produce an air flow 58 along a left side of occupant 90 having a second temperature lower than the first to inform occupant 90 of a right turn of vehicle 100. In some embodiments, the first and second temperatures are reversed, and this may depend on the temperature of the surrounding environment. In some embodiments, a variable-temperature mat 51 is integrated into vehicle seat 92. Variable-temperature mat 51 is configured to produce varying temperatures along a right-side portion 53 and a left-side portion 55 corresponding to the relative temperatures of air flows 56, 58.

As shown in FIGS. 11 and 12, right-side and left-side fans 52, 54 are integrated into a front-row seat 92 of vehicle 100. In some embodiments, right-side and left-side fans 52, 54 are part of a HVAC system of vehicle 100 and integrated into other portions of cabin 101. In some embodiments, right-side and left-side fans 52, 54 are arranged in front of each seating position within cabin 101 as part of air flow system 16. In some embodiments, air flow system 16 includes fans 57 integrated into head rests 98 and a restraint fan 59 coupled to a restraint (e.g., seat belt) of vehicle 100 as shown in FIG. 13. Fans 57 can be operated in similar fashion to fans 52, 54. Restraint fan 59 is configured to direct air flow and/or aromas toward the face of occupant 90.

One embodiment of engagement system 18 in accordance with the present disclosure is shown in FIG. 14. Engagement system 18 is configured to produce tactile engagement with occupant 90 indicative of change in movement 13. Engagement system 18 includes a plurality of right-side motion points 62 arranged along a right side of vehicle seat 92 and a plurality of left-side motion points 64 arranged along a left side of vehicle seat 92. In one illustrative embodiment, right-side motion points 62 are configured to move and engage with occupant 90 to inform occupant 90 of a right turn of vehicle 100. Similarly, left-side motion points 64 are configured to move and engage with occupant 90 to inform occupant 90 of a left turn of vehicle 100.

In another illustrative embodiment, motion points 62, 64 engage with occupant 90 in sequence in a direction 66 from front 102 toward rear 104 of cabin 101 to indicate acceleration of vehicle 100 as suggested in FIG. 15. Similarly, motion points 62, 64 engage with occupant 90 in sequence in a direction from rear 104 toward front 102 of cabin 101 to indicate deceleration of vehicle 100. In some embodiments, motion points 62, 64 are in the form of inflatable bladders that expand and contract as shown in FIG. 16. In some embodiments, motion points 62, 64 are in the form of vibration mechanisms configured to generate vibrations.

Another embodiment of engagement system 18 in accordance with the present disclosure is shown in FIG. 17. Engagement system 18 is configured to produce tactile engagement with occupant 90 indicative of change in movement 13. Engagement system 18 includes at least one of a movable foot support 72 mounted to a floor of vehicle 100 and variable engagement pads 74 integrated into vehicle seat 92. Variable engagement pads 74 include seat-bottom bolster pads 71 and seat-bottom center pads 73 mounted to seat bottom 94, and seat-back bolster pads 75 and seat-back center pads 77 mounted to seat back 96 as shown in FIG. 18. Seat-bottom bolster pads 71 and seat-back bolster pads 75 are positioned along both sides of vehicle seat 92. Movable foot support 72 includes a right-side pedal 76 and a left-side pedal 78 mounted to a base 79 for rotation about an axis A as shown in FIG. 19. Motors, pistons, or other actuation mechanisms move pedals 76, 78 relative to base 79.

In one illustrative embodiment, movable foot support 72 tilts the feet of occupant 90 to the right, pads 71, 75 along a right side of vehicle seat 92 soften, and pads 71, 75 along a left side of vehicle seat 92 harden to inform occupant 90 of a right turn and reposition the body of occupant 90 to absorb the forces of the turn. Similarly, the engagement system 18 repositions the body of occupant toward left side 108 of cabin 101 to indicate a left turn. In another illustrative embodiment, center pads 73 soften and center pads 77 harden to inform occupant 90 of acceleration of vehicle 100. Similarly, center pads 77 soften and center pads 73 harden to inform occupant 90 of deceleration of vehicle 100.

An illustrative process 200 in accordance with the present disclosure for using motion-sickness mitigation system 10 is shown in FIG. 20. The process starts at step 201 and moves to step 202 where motion-sickness mitigation system 10 monitors for motion inputs 15 using control system 11. Monitoring is continued if no motion inputs 15 are detected as suggested at step 204. In response to a motion input 15 being detected, control system 11 identifies the type of change in movement 13 based on the detected motion input 15 as suggested at step 206. For example, rotating the steering wheel to the right leads to a change in movement 13 of a right turn. A signal indicating change in movement 13 is sent by control system 11 to sensory feedback system 12 as suggested at step 208. Sensory feedback system 12 generates an alert indicative of change in movement 13 to inform occupant 90 so that a likelihood of occupant 90 becoming motion-sick is reduced as suggested at step 209. Control system 11 continues to monitor for changes in movement 13.

In illustrative embodiments, motion-sickness mitigation system 10 is useful in reducing a likelihood that an occupant 90 of a vehicle 100 becomes motion sick due to changes in movement 13 of vehicle 100. Occupants can become distracted and unaware of their surroundings, such as by reading or watching content on an electronic device, which can lead to the onset of motion-sickness due to unknown changes in movement of the vehicle they are riding in. This is especially true with the rise of autonomous vehicles. Motion-sickness mitigation system 10 generates alerts to inform occupant 90 of changes in movement 13 to reduce the likelihood of occupant 90 becoming motion sick.

The following numbered clauses include embodiments that are contemplated and non-limiting:

Clause 1. A motion-sickness mitigation system for use in a vehicle, the system comprising a vehicle.

Clause 2. The motion-sickness mitigation system of clause 1, any other clause, or any combination of clauses, further comprising a control system configured to monitor for motion input including at least one of a concurrent, an anticipated, or an instructed change in movement of the vehicle.

Clause 3. The motion-sickness mitigation system of clause 2, any other clause, or any combination of clauses, wherein the control system is configured to produce a signal indicative of the change in movement in response to detecting the motion input.

Clause 4. The motion-sickness mitigation system of clause 3, any other clause, or any combination of clauses, further comprising a sensory feedback system configured to provide means for generating at least one of a tactile, visual, audial, and/or olfactory alert indicative of the change in movement to inform an occupant of the vehicle of the change in movement in response to receiving the signal from the control system to reduce a likelihood of the occupant becoming motion-sick.

Clause 5. The motion-sickness mitigation system of clause 3, any other clause, or any combination of clauses, further comprising a sensory feedback system configured to generate at least one of a tactile, visual, audial, and/or olfactory alert indicative of the change in movement to inform an occupant of the vehicle of the change in movement in response to receiving the signal from the control system to reduce a likelihood of the occupant becoming motion-sick.

Clause 6. The motion-sickness mitigation system of clause 5, any other clause, or any combination of clauses, wherein the sensory feedback system includes a lighting system configured to illuminate a right-side portion of a cabin of the vehicle in response to the signal received from the control system being indicative of a right turn of the vehicle.

Clause 7. The motion-sickness mitigation system of clause 6, any other clause, or any combination of clauses, wherein the lighting system is configured to illuminate a left-side portion of the cabin in response to the signal received from the control system being indicative of a left turn of the vehicle.

Clause 8. The motion-sickness mitigation system of clause 7, any other clause, or any combination of clauses, wherein the lighting system is configured to provide a moving point of illumination from a front of the cabin toward a rear of the cabin in response to the signal received from the control system being indicative of an increase in speed of the vehicle.

Clause 9. The motion-sickness mitigation system of clause 8, any other clause, or any combination of clauses, wherein the lighting system is configured to provide a moving point of illumination from the rear of the cabin toward the front of the cabin in response to the signal received from the control system being indicative of a decrease in speed of the vehicle.

Clause 10. The motion-sickness mitigation system of clause 5, any other clause, or any combination of clauses, wherein the sensory feedback system includes a lighting system configured to illuminate a cabin of the vehicle with a first color.

Clause 11. The motion-sickness mitigation system of clause 10, any other clause, or any combination of clauses, wherein the lighting system is configured to illuminate the cabin with a second color different than the first color in response to the signal received from the control system being indicative of a change in speed of the vehicle.

Clause 12. The motion-sickness mitigation system of clause 11, any other clause, or any combination of clauses, wherein the second color has a relatively longer wavelength in the electromagnetic spectrum than the first color when the change in speed is an increase in speed.

Clause 13. The motion-sickness mitigation system of clause 12, any other clause, or any combination of clauses, and wherein the second color has a relatively shorter wavelength than the first color when the change in speed is decrease in speed.

Clause 14. The motion-sickness mitigation system of clause 11, any other clause, or any combination of clauses, wherein the second color has a relatively shorter wavelength in the electromagnetic spectrum than the first color when the change in speed is an increase in speed.

Clause 15. The motion-sickness mitigation system of clause 14, any other clause, or any combination of clauses, and wherein the second color has a relatively longer wavelength than the first color when the change in speed is decrease in speed.

Clause 16. The motion-sickness mitigation system of clause 5, any other clause, or any combination of clauses, wherein the sensory feedback system includes an indicator system configured to provide indicia to the occupant corresponding to the change in movement of the vehicle in response to the signal received from the control system.

Clause 17. The motion-sickness mitigation system of clause 5, any other clause, or any combination of clauses, wherein the indicia is one of a right-turn arrow, a left-turn arrow, an upward extending arrow, and/or a downward extending arrow.

Clause 18. The motion-sickness mitigation system of clause 5, any other clause, or any combination of clauses, wherein the sensory feedback system includes a sound system configured to provide sound along a right-side portion of a cabin of the vehicle in response to receiving the signal indicative of a right turn of the vehicle.

Clause 19. The motion-sickness mitigation system of clause 18, any other clause, or any combination of clauses, wherein the sound system is configured to provide sound along a left-side portion of the cabin in response to the signal received from the control system being indicative of a left turn of the vehicle.

Clause 20. The motion-sickness mitigation system of clause 19, any other clause, or any combination of clauses, wherein the sound system is configured to provide sound of increasing volume in response to the signal received from the control system being indicative of an increase in speed of the vehicle.

Clause 21. The motion-sickness mitigation system of clause 20, any other clause, or any combination of clauses, wherein the sound system is configured to provide sound of decreasing volume in response to the signal received from the control system being indicative of a decrease in speed of the vehicle.

Clause 22. The motion-sickness mitigation system of clause 5, any other clause, or any combination of clauses, wherein the sensory feedback system includes a ventilation system configured to provide air flow along a right side of the occupant in response to the signal received from the control system being indicative of a right turn of the vehicle.

Clause 23. The motion-sickness mitigation system of clause 22, any other clause, or any combination of clauses, wherein the ventilation system is configured to provide air flow along a left side of the occupant in response to the signal received from the control system being indicative of a left turn of the vehicle.

Clause 24. The motion-sickness mitigation system of clause 23, any other clause, or any combination of clauses, wherein the ventilation system is configured to provide air flow of increasing volume in response to the signal received from the control system being indicative of an increase in speed of the vehicle.

Clause 25. The motion-sickness mitigation system of clause 24, any other clause, or any combination of clauses, and wherein the ventilation system is configured to provide air flow of decreasing volume in response to the signal received from the control system being indicative of a decrease in speed of the vehicle.

Clause 26. The motion-sickness mitigation system of clause 5, any other clause, or any combination of clauses, wherein the sensory feedback system includes an engagement system that comprises a first plurality of inflatable bladders arranged along a right-side portion of a vehicle seat supporting the occupant and a second plurality of inflatable bladders arranged along a left-side portion of the vehicle seat and wherein the first plurality of inflatable bladders is configured to inflate in response to the signal received from the control system being indicative of a right turn of the vehicle.

Clause 27. The motion-sickness mitigation system of clause 26, any other clause, or any combination of clauses, wherein the second plurality of inflatable bladders is configured to inflate in response to the signal received from the control system being indicative of a left turn of the vehicle.

Clause 28. The motion-sickness mitigation system of clause 27, any other clause, or any combination of clauses, wherein the first and second plurality of inflatable bladders are configured to inflate in a sequence moving in a direction from a front of the cabin toward a rear of the cabin in response to the signal received from the control system being indicative of an increase in speed of the vehicle.

Clause 29. The motion-sickness mitigation system of clause 28, any other clause, or any combination of clauses, wherein the first and second plurality of inflatable bladders are configured to inflate in a sequence moving in a direction from the rear of the cabin toward the front of the cabin in response to the signal received from the control system being indicative of a decrease in speed of the vehicle.

Clause 30. The motion-sickness mitigation system of clause 5, any other clause, or any combination of clauses, wherein the sensory feedback system includes an engagement system that comprises a first plurality of vibration generators arranged along a right-side portion of a vehicle seat supporting the occupant and a second plurality of vibration generators arranged along a left-side portion of the vehicle seat and wherein the first plurality of vibration generators is configured to vibrate in response to the signal received from the control system being indicative of a right turn of the vehicle.

Clause 31. The motion-sickness mitigation system of clause 30, any other clause, or any combination of clauses, wherein the second plurality of vibration generators is configured to vibrate in response to the signal received from the control system being indicative of a left turn of the vehicle.

Clause 32. The motion-sickness mitigation system of clause 31, any other clause, or any combination of clauses, wherein the first and second plurality of vibration generators are configured to vibrate in a sequence moving in a direction from a front of the cabin toward a rear of the cabin in response to the signal received from the control system being indicative of an increase in speed of the vehicle.

Clause 33. The motion-sickness mitigation system of clause 32, any other clause, or any combination of clauses, wherein the first and second plurality of vibration generators are configured to vibrate in a sequence moving in a direction from the rear of the cabin toward the front of the cabin in response to the signal received from the control system being indicative of a decrease in speed of the vehicle.

Clause 34. The motion-sickness mitigation system of clause 5, any other clause, or any combination of clauses, further comprising a vehicle seat configured to support the occupant on a support surface thereof, wherein the vehicle seat includes a seat bottom and a seat back.

Clause 35. The motion-sickness mitigation system of clause 34, any other clause, or any combination of clauses, wherein an engagement system of the sensory feedback system comprises variable engagement pads included in right-side and left-side bolsters of the seat bottom and seat back and in central portions of the seat bottom and seat back.

Clause 36. The motion-sickness mitigation system of clause 35, any other clause, or any combination of clauses, wherein the variable engagement pads are configured to alter the support surface on the right-side bolsters in response to the signal received from the control system being indicative of a right turn of the vehicle.

Clause 37. The motion-sickness mitigation system of clause 36, any other clause, or any combination of clauses, wherein the variable engagement pads are configured to alter the support surface on the left-side bolsters in response to the signal received from the control system being indicative of a left turn of the vehicle.

Clause 38. The motion-sickness mitigation system of clause 37, any other clause, or any combination of clauses, wherein the variable engagement pads are configured to alter the support surface on the central portion of the seat back in response to the signal received from the control system being indicative of an increase in speed of the vehicle.

Clause 39. The motion-sickness mitigation system of clause 38, any other clause, or any combination of clauses, wherein the variable engagement pads are configured to alter the support surface on the central portion of the seat bottom in response to the signal received from the control system being indicative of a decrease in speed of the vehicle.

Clause 40. A motion-sickness mitigation system for use in a vehicle, the system comprising
a control system configured to monitor for motion inputs including at least one of a concurrent, an anticipated, or an instructed change in movement of the vehicle.

Clause 41. The motion-sickness mitigation system of clause 40, any other clause, or any combination of clauses, wherein the control system is configured to produce a signal indicative of the change in movement in response to detecting a motion input.

Clause 42. The motion-sickness mitigation system of clause 41, any other clause, or any combination of clauses, further comprising a sensory feedback system configured to generate an alert indicative of the change in movement to inform an occupant of the vehicle of the change in movement in response to receiving the signal from the control system to reduce a likelihood of the occupant becoming motion-sick.

Clause 43. The motion-sickness mitigation system of clause 42, any other clause, or any combination of clauses, further comprising a lighting system configured to provide illumination within the cabin of the vehicle.

Clause 44. The motion-sickness mitigation system of clause 43, any other clause, or any combination of clauses, wherein the lighting system is configured to adjust the illumination in response to the signal received from the control system.

Clause 45. The motion-sickness mitigation system of clause 44, any other clause, or any combination of clauses, wherein the lighting system is configured to illuminate a right-side portion of the cabin in response to receiving a signal indicating a right turn of the vehicle.

Clause 46. The motion-sickness mitigation system of clause 45, any other clause, or any combination of clauses, wherein the lighting system is configured to illuminate a left-side portion of the cabin in response to receiving a signal indicating a left turn of the vehicle.

Clause 47. The motion-sickness mitigation system of clause 43, any other clause, or any combination of clauses, wherein the lighting system is configured to provide a moving point of illumination from a front of the cabin toward a rear of the cabin in response to receiving a signal indicating an increase in speed of the vehicle.

Clause 48. The motion-sickness mitigation system of clause 47, any other clause, or any combination of clauses, wherein the lighting system is configured to provide a moving point of illumination from the rear of the cabin toward the front of the cabin in response to receiving a signal indicating a decrease in speed of the vehicle.

Clause 49. The motion-sickness mitigation system of clause 43, any other clause, or any combination of clauses, wherein the lighting system is configured to illuminate the cabin with a first color and a second color different than the first color in response to receiving a signal indicating a change in speed of the vehicle.

Clause 50. The motion-sickness mitigation system of clause 49, any other clause, or any combination of clauses, wherein the second color is a relatively warmer color than the first color when the change in speed is an increase in speed, and wherein the second color is a relatively cooler color than the first color when the change in speed is decrease in speed.

Clause 51. The motion-sickness mitigation system of clause 42, any other clause, or any combination of clauses, further comprising an indicator system configured to provide indicia to the occupant corresponding to the change in movement of the vehicle in response to the signal received from the control system.

Clause 52. The motion-sickness mitigation system of clause 51, any other clause, or any combination of clauses, wherein the indicia is one of a right-turn arrow, a left-turn arrow, a upward extending arrow, and a downward extending arrow.

Clause 53. The motion-sickness mitigation system of clause 42, any other clause, or any combination of clauses, further comprising a sound system, wherein the sound system is configured to provide sound within the cabin of the vehicle.

Clause 54. The motion-sickness mitigation system of clause 53, any other clause, or any combination of clauses, wherein the sound system is configured to adjust the sound in response to the signal received from the control system.

Clause 55. The motion-sickness mitigation system of clause 53, any other clause, or any combination of clauses, wherein the sound system is configured to provide sound along a right-side portion of the cabin in response to receiving a signal indicating a right turn of the vehicle.

Clause 56. The motion-sickness mitigation system of clause 55, any other clause, or any combination of clauses, wherein the sound system is configured to provide sound along a left-side portion of the cabin in response to receiving a signal indicating a left turn of the vehicle.

Clause 57. The motion-sickness mitigation system of clause 53, any other clause, or any combination of clauses, wherein the sound system is configured to provide sound of increasing volume in response to receiving a signal indicating an increase in speed of the vehicle, and wherein the sound system is configured to provide sound of decreasing volume in response to receiving a signal indicating a decrease in speed of the vehicle.

Clause 58. The motion-sickness mitigation system of clause 42, any other clause, or any combination of clauses, further comprising a ventilation system, wherein the ventilation system is configured to provide air flow within the cabin of the vehicle.

Clause 59. The motion-sickness mitigation system of clause 58, any other clause, or any combination of clauses, wherein the ventilation system is configured to adjust the air flow in response to the signal received from the control system.

Clause 60. The motion-sickness mitigation system of clause 58, any other clause, or any combination of clauses, wherein the ventilation system is configured to provide air flow along a right side of the occupant in response to receiving a signal indicating a right turn of the vehicle.

Clause 61. The motion-sickness mitigation system of clause 60, any other clause, or any combination of clauses, wherein the ventilation system is configured to provide air flow along a left side of the occupant in response to receiving a signal indicating a left turn of the vehicle.

Clause 62. The motion-sickness mitigation system of clause 58, any other clause, or any combination of clauses, wherein the ventilation system is configured to provide air flow of increasing volume in response to receiving a signal indicating an increase in speed of the vehicle, and wherein the ventilation system is configured to provide air flow of decreasing volume in response to receiving a signal indicating a decrease in speed of the vehicle.

Clause 63. The motion-sickness mitigation system of clause 42, any other clause, or any combination of clauses, further comprising an engagement system, wherein the engagement system is configured to engage with the occupant.

Clause 64. The motion-sickness mitigation system of clause 63, any other clause, or any combination of clauses, wherein the engagement system is configured to adjust the engagement with the occupant in response to the signal received from the control system.

Clause 65. The motion-sickness mitigation system of clause 63, any other clause, or any combination of clauses, wherein the engagement system comprises a first plurality of inflatable bladders arranged along a right-side portion of a vehicle seat supporting the occupant.

Clause 66. The motion-sickness mitigation system of clause 65, any other clause, or any combination of clauses, wherein the engagement system further comprises a second plurality of inflatable bladders arranged along a left-side portion of the vehicle seat.

Clause 67. The motion-sickness mitigation system of clause 66, any other clause, or any combination of clauses, wherein the first plurality of inflatable bladders is configured to inflate in response to receiving a signal indicating a right turn of the vehicle.

Clause 68. The motion-sickness mitigation system of clause 67, any other clause, or any combination of clauses, wherein the second plurality of inflatable bladders is configured to inflate in response to receiving a signal indicating a left turn of the vehicle.

Clause 69. The motion-sickness mitigation system of clause 68, any other clause, or any combination of clauses, wherein the first and second plurality of inflatable bladders are configured to inflate in a sequence moving in a direction from a front of the cabin toward a rear of the cabin in response to receiving a signal indicating an increase in speed of the vehicle.

Clause 70. The motion-sickness mitigation system of clause 69, any other clause, or any combination of clauses, wherein the first and second plurality of inflatable bladders are configured to inflate in a sequence moving in a direction from the rear of the cabin toward the front of the cabin in response to receiving a signal indicating a decrease in speed of the vehicle.

Clause 71. The motion-sickness mitigation system of clause 63, any other clause, or any combination of clauses, wherein the engagement system comprises a first plurality of vibration generators arranged along a right-side portion of a vehicle seat supporting the occupant.

Clause 72. The motion-sickness mitigation system of clause 71, any other clause, or any combination of clauses, wherein the engagement system further comprises a second plurality of vibration generators arranged along a left-side portion of the vehicle seat.

Clause 73. The motion-sickness mitigation system of clause 72, any other clause, or any combination of clauses, wherein the first plurality of vibration generators is configured to vibrate in response to receiving a signal indicating a right turn of the vehicle.

Clause 74. The motion-sickness mitigation system of clause 73, any other clause, or any combination of clauses, wherein the second plurality of vibration generators is configured to vibrate in response to receiving a signal indicating a left turn of the vehicle.

Clause 75. The motion-sickness mitigation system of clause 74, any other clause, or any combination of clauses, wherein the first and second plurality of vibration generators are configured to vibrate in a sequence moving in a direction from a front of the cabin toward a rear of the cabin in response to receiving a signal indicating an increase in speed of the vehicle and wherein the first and second plurality of vibration generators are configured to vibrate in a sequence moving in a direction from the rear of the cabin toward the front of the cabin in response to receiving a signal indicating a decrease in speed of the vehicle.

Clause 76. The motion-sickness mitigation system of clause 63, any other clause, or any combination of clauses, further comprising a vehicle seat configured to support the occupant on a support surface thereof, wherein the vehicle seat includes a seat bottom and a seat back, wherein the engagement system comprises variable engagement pads included in right-side and left-side bolsters of the seat bottom and seat back and in central portions of the seat bottom and seat back.

Clause 77. The motion-sickness mitigation system of clause 76, any other clause, or any combination of clauses, wherein the variable engagement pads are configured to alter the support surface on the right-side bolsters in response to receiving a signal indicating a right turn of the vehicle.

Clause 78. The motion-sickness mitigation system of clause 77, any other clause, or any combination of clauses, wherein the variable engagement pads are configured to alter the support surface on the left-side bolsters in response to receiving a signal indicating a left turn of the vehicle.

Clause 79. The motion-sickness mitigation system of clause 78, any other clause, or any combination of clauses, wherein the variable engagement pads are configured to alter the support surface on the central portion of the seat back in response to receiving a signal indicating an increase in speed of the vehicle.

Clause 80. The motion-sickness mitigation system of clause 76, any other clause, or any combination of clauses, wherein the variable engagement pads are configured to alter the support surface on the central portion of the seat bottom in response to receiving a signal indicating a decrease in speed of the vehicle.

Clause 81. The motion-sickness mitigation system of clause 63, any other clause, or any combination of clauses, wherein a movable foot support included in the engagement system comprises a right-side pedal and a left-side pedal.

Clause 82. The motion-sickness mitigation system of clause 81, any other clause, or any combination of clauses, wherein the left-side pedal raises and the right-side pedal lowers in response to the engagement system receiving a signal indicating a right turn of the vehicle.

Clause 83. The motion-sickness mitigation system of clause 82, any other clause, or any combination of clauses, wherein the right-side pedal raises and the left-side pedal lowers in response to the engagement system receiving a signal indicating a left turn of the vehicle.

Clause 84. A method for reducing a likelihood of motion-sickness of an occupant of a vehicle, the method comprising
monitoring with a control system for motion inputs including at least one of a concurrent, an anticipated, and an instructed change in movement of the vehicle.

Clause 85. The method of clause 84, any other clause, or any combination of clauses, further comprising the step of producing with the control system a signal indicative of the change in movement in response to detecting a motion input.

Clause 86. The method of clause 85, any other clause, or any combination of clauses, further comprising receiving with a sensory feedback system the signal produced by the control system.

Clause 87. The method of clause 86, any other clause, or any combination of clauses, further comprising generating with the sensory feedback system an alert indicative of the change in movement to inform the occupant of the change in movement in response to receiving the signal from the control system to reduce a likelihood of the occupant becoming motion-sick.

Clause 88. The method of clause 87, any other clause, or any combination of clauses, wherein generating the alert with the sensory feedback system includes illuminating a right-side portion of a cabin of the vehicle in response to the sensory feedback system receiving a signal indicating a right turn of the vehicle.

Clause 89. The method of clause 88, any other clause, or any combination of clauses, further comprising illuminating a left-side portion of the cabin in response to the sensory feedback system receiving a signal indicating a left turn of the vehicle.

Clause 90. The method of clause 89, any other clause, or any combination of clauses, further comprising providing a moving point of illumination from a front of the cabin toward a rear of the cabin in response to the sensory feedback system receiving a signal indicating an increase in speed of the vehicle.

Clause 91. The method of clause 90, any other clause, or any combination of clauses, further comprising providing a moving point of illumination from the rear of the cabin toward the front of the cabin in response to the sensory feedback system receiving a signal indicating a decrease in speed of the vehicle.

Clause 92. The method of clause 87, wherein generating the alert with the sensory feedback system includes illuminating a cabin of the vehicle with a first color.

Clause 93. The method of clause 92, any other clause, or any combination of clauses, further comprising illuminating the cabin with a second color different than the first color in response to the sensory feedback system receiving a signal indicating a change in speed of the vehicle.

Clause 94. The method of clause 93, any other clause, or any combination of clauses, wherein the second color has a relatively longer wavelength in the electromagnetic spectrum than the first color when the change in speed is an increase in speed.

Clause 95. The method of clause 94, any other clause, or any combination of clauses, wherein the second color has a relatively shorter wavelength than the first color when the change in speed is decrease in speed.

Clause 96. The method of clause 93, any other clause, or any combination of clauses, wherein the second color has a relatively longer wavelength in the electromagnetic spectrum than the first color when the change in speed is an increase in speed.

Clause 97. The method of clause 94, any other clause, or any combination of clauses, wherein the second color has a relatively shorter wavelength than the first color when the change in speed is an increase in speed.

Clause 97. The method of clause 96, any other clause, or any combination of clauses, wherein generating the alert with the sensory feedback system includes providing indicia to the occupant corresponding to the change in movement of the vehicle in response to the signal received from the control system, and wherein the indicia is one of a right-turn arrow, a left-turn arrow, a upward extending arrow, and a downward extending arrow.

Clause 98. The method of clause 87, any other clause, or any combination of clauses, wherein generating the alert with the sensory feedback system includes providing sound along a right-side portion of a cabin of the vehicle in response to the sensory feedback system receiving a signal indicating a right turn of the vehicle.

Clause 99. The method of clause 98, any other clause, or any combination of clauses, wherein generating the alert with the sensory feedback system further includes providing sound along a left-side portion of the cabin in response to the sensory feedback system receiving a signal indicating a left turn of the vehicle.

Clause 100. The method of clause 99, any other clause, or any combination of clauses, wherein generating the alert with the sensory feedback system further includes providing sound of increasing volume in response to the sensory feedback system receiving a signal indicating an increase in speed of the vehicle.

Clause 101. The method of clause 100, any other clause, or any combination of clauses, wherein generating the alert with the sensory feedback system further includes providing sound of decreasing volume in response to the sensory feedback system receiving a signal indicating a decrease in speed of the vehicle.

Clause 102. The method of clause 87, any other clause, or any combination of clauses, wherein generating the alert with the sensory feedback system includes providing air flow along a right side of the occupant in response to the sensory feedback system receiving a signal indicating a right turn of the vehicle.

Clause 103. The method of clause 102, any other clause, or any combination of clauses, wherein generating the alert with the sensory feedback system further includes providing air flow along a left side of the occupant in response to the sensory feedback system receiving a signal indicating a left turn of the vehicle.

Clause 104. The method of clause 103, any other clause, or any combination of clauses, wherein generating the alert with the sensory feedback system further includes providing air flow of increasing volume in response to the sensory feedback system receiving a signal indicating an increase in speed of the vehicle.

Clause 105. The method of clause 104, any other clause, or any combination of clauses, wherein generating the alert with the sensory feedback system further includes providing air flow of decreasing volume in response to the sensory feedback system receiving a signal indicating a decrease in speed of the vehicle.

Clause 106. The method of clause 87, any other clause, or any combination of clauses, wherein generating the alert with the sensory feedback system includes activating a plurality of motion points along a right side of the occupant in response to the sensory feedback system receiving a signal indicating a right turn of the vehicle.

Clause 108. The method of clause 107, any other clause, or any combination of clauses, wherein generating the alert with the sensory feedback system further includes activating a plurality of motion points along a left side of the occupant in response to the sensory feedback system receiving a signal indicating a left turn of the vehicle.

Clause 109. The method of clause 108, any other clause, or any combination of clauses, wherein generating the alert with the sensory feedback system further includes activating a plurality of motion points in sequence in a direction extending from a front of the cabin toward a rear of the cabin in response to the sensory feedback system receiving a signal indicating an increase in speed of the vehicle.

Clause 110. The method of clause 109, any other clause, or any combination of clauses, wherein generating the alert with the sensory feedback system further includes activating a plurality of motion points in sequence in a direction extending from the rear of the cabin toward the front of the cabin in response to the sensory feedback system receiving a signal indicating a decrease in speed of the vehicle.

The invention claimed is:

1. A motion-sickness mitigation system comprising a vehicle, a control system configured to monitor for motion input including at least one of a concurrent, an anticipated, or an instructed change in movement of the vehicle, the control system configured to produce a signal indicative of the change in movement in response to detecting the motion input, and a sensory feedback system configured to generate at least one of a tactile, visual, audial, and olfactory alert indicative of the change in movement to inform an occupant of the vehicle of the change in movement in response to receiving the signal from the control system to reduce a likelihood of the occupant becoming motion-sick,
wherein the sensory feedback system includes an engagement system that comprises a first plurality of inflatable bladders arranged along a right-side portion of a vehicle seat supporting the occupant and a second plurality of inflatable bladders arranged along a left-side portion of the vehicle seat, wherein the first plurality of inflatable bladders is configured to inflate in response to the signal received from the control system being indicative of a right turn of the vehicle, wherein the second plurality of inflatable bladders is configured to inflate in response to the signal received from the control system being indicative of a left turn of the vehicle, wherein the first and second plurality of inflatable bladders are configured to inflate in a sequence moving in a direction from a front of a cabin of the vehicle toward a rear of the cabin in response to the signal received from the control system being indicative of an increase in speed of the vehicle, and wherein the first and second plurality of inflatable bladders are configured to inflate in a sequence moving in a direction from the rear of the cabin toward the front of the cabin in response to the signal received from the control system being indicative of a decrease in speed of the vehicle.

2. The motion-sickness mitigation system of claim 1, wherein the sensory feedback system further includes a lighting system configured to illuminate a right-side portion of the cabin of the vehicle in response to the signal received from the control system being indicative of a right turn of the vehicle, wherein the lighting system is configured to illuminate the left-side portion of the cabin in response to the signal received from the control system being indicative of a left turn of the vehicle, wherein the lighting system is configured to provide a moving point of illumination from the front of the cabin toward a rear of the cabin in response to the signal received from the control system being indicative of an increase in speed of the vehicle, and wherein the lighting system is configured to provide a moving point of illumination from the rear of the cabin toward the front of the cabin in response to the signal received from the control system being indicative of a decrease in speed of the vehicle.

3. The motion-sickness mitigation system of claim 1, wherein the sensory feedback system further includes a lighting system configured to illuminate the cabin of the vehicle with a first color, wherein the lighting system is configured to illuminate the cabin with a second color different than the first color in response to the signal received from the control system being indicative of a change in speed of the vehicle, wherein the second color has a relatively longer wavelength in the electromagnetic spectrum than the first color when the change in speed is the increase in speed, and wherein the second color has a relatively shorter wavelength than the first color when the change in speed is the decrease in speed.

4. The motion-sickness mitigation system of claim 1, wherein the sensory feedback system includes an indicator system configured to provide indicia to the occupant corresponding to the change in movement of the vehicle in response to the signal received from the control system and wherein the indicia is one of a right-turn arrow, a left-turn arrow, an upward extending arrow, and a downward extending arrow.

5. The motion-sickness mitigation system of claim 1, wherein the sensory feedback system further includes a sound system configured to provide sound along the right-side portion of the cabin of the vehicle in response to receiving the signal indicative of a right turn of the vehicle, wherein the sound system is configured to provide sound along the left-side portion of the cabin in response to the signal received from the control system being indicative of a left turn of the vehicle, wherein the sound system is configured to provide sound of increasing volume in response to the signal received from the control system being indicative of an increase in speed of the vehicle, and wherein the sound system is configured to provide sound of decreasing volume in response to the signal received from the control system being indicative of a decrease in speed of the vehicle.

6. The motion-sickness mitigation system of claim 1, wherein the sensory feedback system further includes a ventilation system configured to provide air flow along a right side of the occupant in response to the signal received from the control system being indicative of a right turn of the vehicle, wherein the ventilation system is configured to provide air flow along a left side of the occupant in response to the signal received from the control system being indicative of a left turn of the vehicle, wherein the ventilation system is configured to provide air flow of increasing volume in response to the signal received from the control system being indicative of an increase in speed of the vehicle, and wherein the ventilation system is configured to provide air flow of decreasing volume in response to the signal received from the control system being indicative of a decrease in speed of the vehicle.

7. A motion-sickness mitigation system, comprising a vehicle, a control system configured to monitor for motion input including at least one of a concurrent, an anticipated, or an instructed change in movement of the vehicle, the control system configured to produce a signal indicative of the change in movement in response to detecting the motion input, and a sensory feedback system configured to generate at least one of a tactile, visual, audial, and olfactory alert indicative of the change in movement to inform an occupant of the vehicle of the change in movement in response to receiving the signal from the control system to reduce a likelihood of the occupant becoming motion-sick, wherein the sensory feedback system includes an engagement system that comprises a first plurality of vibration generators arranged along a right-side portion of a vehicle seat supporting the occupant and a second plurality of vibration generators arranged along a left-side portion of the vehicle seat, wherein the first plurality of vibration generators is configured to vibrate in response to the signal received from the control system being indicative of a right turn of the vehicle, wherein the second plurality of vibration generators is configured to vibrate in response to the signal received from the control system being indicative of a left turn of the vehicle, wherein the first and second plurality of vibration generators are configured to vibrate in a sequence moving in a direction from a front of a cabin of the vehicle toward a rear of the cabin in response to the signal received from the control system being indicative of an increase in speed of the vehicle, and wherein the first and second plurality of vibration generators are configured to vibrate in a sequence moving in a direction from the rear of the cabin toward the front of the cabin in response to the signal received from the control system being indicative of a decrease in speed of the vehicle.

8. A motion-sickness mitigation system, comprising a vehicle, a control system configured to monitor for motion input including at least one of a concurrent, an anticipated, or an instructed change in movement of the vehicle, the control system configured to produce a signal indicative of the change in movement in response to detecting the motion input, and a sensory feedback system configured to generate at least one of a tactile, visual, audial, and olfactory alert indicative of the change in movement to inform an occupant of the vehicle of the change in movement in response to receiving the signal from the control system to reduce a likelihood of the occupant becoming motion-sick; and a vehicle seat configured to support the occupant on a support surface thereof, wherein the vehicle seat includes a seat bottom and a seat back, wherein an engagement system of the sensory feedback system comprises variable engagement pads included in right-side and left-side bolsters of the seat bottom and seat back and in central portions of the seat bottom and seat back, wherein the variable engagement pads are configured to alter the support surface on the right-side bolsters in response to the signal received from the control system being indicative of a right turn of the vehicle, wherein the variable engagement pads are configured to alter the support surface on the left-side bolsters in response to the signal received from the control system being indicative of a left turn of the vehicle, wherein the variable engagement pads are configured to alter the support surface on a central portion of the seat back in response to the signal received from the control system being indicative of an increase in speed of the vehicle, and wherein the variable engagement pads are configured to alter the support surface on a central portion of the seat bottom in response to the signal received from the control system being indicative of a decrease in speed of the vehicle.

* * * * *